United States Patent [19]
Kramer et al.

[11] Patent Number: 6,069,189
[45] Date of Patent: May 30, 2000

[54] LIGHT-AND BRIGHT-COLORED ANTIFOULING PAINTS

[75] Inventors: Johannes Petrus Kramer, Vinkeveen; Marcel Vos, Huizen, both of Netherlands

[73] Assignee: Sigma Coatings, B.V., Netherlands

[21] Appl. No.: 08/932,673

[22] Filed: Sep. 18, 1997

[30] Foreign Application Priority Data

Sep. 19, 1996 [BE] Belgium ................. 96115024

[51] Int. Cl.[7] ........................................... C08K 5/34
[52] U.S. Cl. ........................................ 523/122; 524/104
[58] Field of Search ..................... 523/122, 104

[56] References Cited

U.S. PATENT DOCUMENTS

| | | | |
|---|---|---|---|
| 2,984,673 | 5/1961 | Bortnick et al. | 524/104 |
| 3,088,837 | 5/1963 | Prescott et al. | 524/104 |
| 3,702,231 | 11/1972 | Spartanburg | 524/104 |
| 4,369,277 | 1/1983 | Wirth et al. | 524/104 |

*Primary Examiner*—Kriellion Sanders
*Attorney, Agent, or Firm*—Michael J. Caddell; M. Norwood Cheairs

[57] ABSTRACT

2-trihalogenomethyl-3-halogeno-4-cyano pyrrole derivatives which are substituted in position 5 and optionally in position 1 are used as barnaclecide in antifouling paints, which can therefore be formulated as light- or bright-colored, particularly as bright white. The halogens in positions 2 and 3 are independently selected from the group consisting of florine, chlorine and bromine, preferably florine in position 2 and bromine in position 3. The substituent in position 5 is selected from the group consisting of C1-8 alkyl, C1-8 monohalogenoalkyl, C5-6 cycloalkyl, C5-6 monohalogenocycloalkyl, benzyl, phenyl, mono- and di-halogeno-benzyl or -phenyl, mono- and di-C1-4 alkyl benzyl or phenyl, and monohalogeno mono-C1-4-alkyl benzyl or phenyl, the halogen being selected from the group consisting of chlorine and bromine, prefereably chlorine; the most preferred substituent in position 5 is parachlorophenyl. The optional substituent in position 1 is selected from the group consisting of C1-4 alkyl and C1-4 alkoxy C1-4 alkyl; it is preferred that no substituent be present in position 1. The most preferred compound for use as barnaclecide in the invention is 2-trifluoromethyl-3-bromo-4-cyano-5-parachlorophenyl pyrrole. Antifouling paints may contain 0.5 to 9.9 wt % of barnaclecide, based on the total weight of the dry mass of the composition, preferably 1 to 6 wt %, most preferably 1.5 to 4 wt %.

8 Claims, No Drawings

LIGHT-AND BRIGHT-COLORED ANTIFOULING PAINTS

The present invention relates to light- or bright-coloured antifouling paints, particularly marine paints. More specifically, it relates to the use of specific barnaclecides that do not interfere with the colour of antifouling paints.

Antifouling paints must be effective against the settlement of the major fouling organisms, particularly on the ship hulls. Among those organisms, barnacles have proved to be the most troublesome because they resist to most biocides; they are probably the most widespread and the principal foulant of ships in ports.

Up to now, only two compounds were available in practice that have an efficient barnaclecide effect. Barnaclecide is used herein as generally defining the prevention of fouling by barnacles, particularly through the toxic effect of the compound on the barnacles themselves or on their larvae.

For a variety of technical reasons, only trialkyltin biocides (more specifically tributyltin and triphenyltin biocides) and cuprous oxide have been available in practice as barnaclecides.

Cuprous thiocyanate, which has sometimes been described as an off-white equivalent to the red-brown coloured cuprous oxide, is more costly (about three times more expensive) and has about half of its efficiency which finally results in a less satisfactory antifouling performance, not to mention the release of copper into the environment. Furthermore, paints containing cuprous thiocyanate cannot be formulated to bright white as the cuprous thiocyanate gives a green-shade, particularly when combined with resinates.

Trialkyltin biocides and cuprous oxide are known to display a double synergy, namely on the general performance (i.e. towards slime, algae and particularly barnacles) and on the stability of the paint, which led to the generalisation of their combined use.

Organotin derivatives are hazardous and toxic at very low concentrations, and it is thus desirable to limit their use. Further, environmental concerns have led to a ban of trialkyltin salts in antifouling paints, while the amount of trialkyltin-containing comonomer in binders had to be strongly reduced. Indeed, concentrations of trialkyltin toxicant can build up sufficiently to affect aquatic life, particularly marine life in harbours or even in bays; also, the potential of tin entrance in the food chain might affect humans.

The reduction in the amount of tin-containing comonomer has obviously led to a reduction of the barnaclecide activity, which in turn led to the need for increased concentrations of cuprous oxide in the antifouling paints. Thus, practically all antifouling paint compositions now contain cuprous oxide, which, because of its red-brown colour, prevents the making of light- or bright-coloured coatings even when present in small amounts. Such light- or bright-coloured coatings are nevertheless demanded by ship owners who wish their ships painted with their light or bright company colours. There is thus a need in the art for low-tin (particularly tin-free) light- or bright-coloured antifouling paints.

Low-tin antifouling paints, as used herein, are paints which do not contain enough tin (in the form of trialkyltin as salt or in comonomers) to show an efficient barnaclecide effect.

The Applicants have now found that certain pyrrole derivatives are efficient barriaclecides and can be used to formulate light- or bright-coloured antifouling paints. More particularly, it is now possible to formulate a bright white antifouling paint.

The compounds for use as barnaclecide in the invention are 2-trihalogenomethyl-3-halogeno-4-cyano pyrrole derivatives which are substituted in position 5 and optionally in position 1. The halogens in positions 2 (i.e. on the 2-methyl substituent) and 3 are independently selected from the group consisting of fluorine, chlorine and bromine, preferably fluorine in position 2 and bromine in position 3. The substituent in position 5 is selected from the group consisting of C1-8 alkyl, C1-8 monohalogenoalkyl, C5-6 cycloalkyl, C5-6 monohalogenocycloalkyl, phenyl, benzyl, mono- and di-halogenobenzyl, mono- and di-halogenophenyl, mono- and di-C1-4-alkyl benzyl, mono- and di-C1-4-alkyl phenyl, monohalogeno mono-C1-4-alkyl benzyl and monohalogeno mono-C1-4-alkyl phenyl, the halogen on the substituent in position 5 being selected from the group consisting of chlorine and bromine, preferably chlorine; the most preferred substituent in position 5 is para-chlorophenyl. The optional substituent in position 1 is selected from the group consisting of C1-4 alkyl and C1-4 alkoxy C1-4 alkyl; it is preferred that no substituent be present in position 1.

The most preferred compound for use as barnaclecide in the invention is 2-trifluoromethyl-3-bromo-4-cyano-5-parachlorophenyl pyrrole. The compound should be used in an amount of 0.5 to 9.9 wt %, based on the total weight of the dry mass of the composition, preferably 1 to 6 wt %, most preferably 1.5 to 4 wt %.

By using the compounds as barnaclecide in an amount of 0.5 to 9.9 wt %, based on the total weight of the dry mass of the composition, in antifouling paints, the Applicants have unexpectedly found that the coatings have an outstanding activity against barnacles; the Applicants further surprisingly found that excellent performances were obtained with amounts as low as 2 wt % (based on the total weight of the dry mass of the composition), thus providing an excellent weight/efficiency ratio in comparison to the systems combining trialkyltin copolymers and cuprous oxide.

The antifouling paint compositions according to the invention essentially comprise as barnaclecide at least one 2-trihalogenomethyl-3-halogeno-4-cyano pyrrole derivative (as described hereabove) in an amount of 0.5 to 9.9 wt %. They further comprise the usual components, it being understood from the preceding description that cuprous oxide can be totally omitted and need not be replaced by cuprous thiocyanate; as the compounds used as barnaclecide according to this invention have little or no algicide effect in the recommended concentration range, it is however essential that the usual components present in addition to the barnaclecide comprise an efficient amount of at least one algicide. Algicides that will not interfere with the making of light- or bright-coloured antifouling paints (and more generally with the making of any colour) are known in the art and need not be described here (typical suitable algicides are given in the examples below). It is most preferred to use an algicide that is also active against slime-causing organisms (including bacteria).

The antifouling paint compositions according to the invention also comprise low-tin paints, i.e. paints which contain an amount of tin (in the form of triorganotin in monomeric units) which is by itself insufficient to show an efficient barnaclecide effect.

The antifouling paint compositions of the invention preferably comprise essentially:

(i) a water-erodible binder polymer having protected acid functionality;

(ii) an efficient amount of an algicide; and (iii) at least one 2-trihalogenomethyl-3-halogeno-4-cyano pyrrole derivative (as described hereabove) in an amount of 0.5 to 9.9 wt %, based on the total weight of the dry mass of the composition.

Water-erodible binder polymers having protected acid functionality are well-known in the art; the latest review can be found in WO-A-9603465. The protected acid functionality can for example be carboxylic acid functionality protected by a divalent metal or organometallic radical bonded to the residue of a monobasic organic acid, a monoamine or quaternary ammonium groups, triorganosilyl groups or triorganotin groups, or sulphonic acid functionality blocked by a monoamine or quaternary ammonium group.

According to a first embodiment, the antifouling paint composition essentially comprises:

(i) a trialkyltin (meth)acrylate copolymer;

(ii) an efficient amount of an algicide; and (iii) at least one 2-trihalogenomethyl-3-halogeno-4-cyano pyrrole derivative (as described hereabove) in an amount of 0.5 to 9.9 wt %, based on the total weight of the dry mass of the composition.

Trialkyltin (meth)acrylate copolymers are well-known in the art of self-polishing paints since GB-A-1457590 and need thus not be described here. Paint compositions according to the first embodiment are particularly useful when a low-tin copolymer is used.

According to a second embodiment, the antifouling paint composition essentially comprises:

(i) a first component selected from one or more rosin-based components;

(ii) a (co)polymer as binder;

(iii) an efficient amount of an algicide; and (iv) at least one 2-trihalogenomethyl-3-halogeno-4-cyano pyrrole derivative (as described hereabove) in an amount of 0.5 to 9.9 wt %, based on the total weight of the dry mass of the composition.

According to a third embodiment, the antifouling paint composition essentially comprises:

(i) a first component selected from one or more rosin-based components;

(ii) a plasticiser;

(iii) an efficient amount of an algicide; and (iv) at least one 2-trihalogenomethyl-3-halogeno-4-cyano pyrrole derivative (as described hereabove) in an amount of 0.5 to 9.9 wt %, based on the total weight of the dry mass of the composition.

Plasticisers are well-known; the most commonly used in antifouling paints are chlorinated paraffins.

According to a fourth embodiment, the antifouling paint composition essentially comprises:

(i) a first component selected from one or more rosin-based components;

(ii) a hydrophilic binder;

(iii) an efficient amount of an algicide; and (iv) at least one 2-trihalogenomethyl-3-halogeno-4-cyano pyrrole derivative (as described hereabove) in an amount of 0.5 to 9.9 wt %, based on the total weight of the dry mass of the composition.

Hydrophilic binders suitable for use in such compositions are well-known in the art; they are exemplified by the copolymers disclosed in EP-A-289481 and EP-A-526441.

According to a fifth embodiment, the antifouling paint composition essentially comprises:

(i) a (co)polymer based on copper acrylate;

(ii) optionally, one or more rosin-based components;

(iii) an efficient amount of an algicide; and (iv) at least one 2-trihalogenomethyl-3-halogeno-4-cyano pyrrole derivative (as described hereabove) in an amount of 0.5 to 9.9 wt %, based on the total weight of the dry mass of the composition.

Copper acrylate based (co)polymers are well known in the art; they are exemplified by those disclosed in U.S. Pat. No. 5,236,493.

Rosin is a loosely used term, denoting the result of a harvesting of the gum exudations from surface cuts made in certain species of trees. Rosin is usually defined as the product obtained from pines; similar products include congo, damar, kauri and manila gums. Other processes for obtaining rosin include dissolving wood rosin from pine stumps after forests have been felled, or refining a by-product of the Kraft paper manufacturing process to produce tall oil rosin.

Pine-originating rosin is preferably chosen, although similar products may be contemplated providing they have a similar hydrophilic/lipophilic balance.

The main component (about 80 wt %) of rosin is abietic acid, also called sylvic acid (Chemical Abstracts Service Registry Number: 514-10-3), which could be used instead of rosin.

The preferred rosin-based components are rosin itself, its copper or zinc derivatives, hereinafter called copper resinate and zinc resinate, other resinate salts having a comparable solubility, or mixtures thereof. The salts are prepared by any known methods, typically by metathesis with the metal carbonate, oxide, hydroxide or hydroxycarbonate (whether in situ or in a separate reaction). In some case, the transformation of abietic acid into salts thereof may upgrade properties like the melting point, hardness, durability, water or solvent resistance.

The paint compositions according to the invention may also comprise sparingly soluble metalliferous pigments, pigments which are highly insoluble in sea-water, dyes, fillers, any other biocides, and/or any additive. Through an appropriate selection, which is easily made by a man skilled in the art on the basis of his knowledge of the colour provided by each component, any light- or bright-coloured paint can be prepared.

The metalliferous pigment sparingly soluble in sea-water is exemplified by cuprous thiocyanate, cuprous oxide and zinc oxide. The paint preferably includes no cuprous oxide. These pigments have a sea-water solubility such that the pigment particles do not survive at the paint surface. The pigment is believed to have the effect of inducing the overall smoothing which the relatively-moving sea-water exerts on the paint film.

The paint composition may additionally contain a pigment which is highly insoluble in sea-water, such as titanium dioxide or iron oxide. Such highly insoluble pigments can be used at up to 40 percent by weight of the total pigment component of the paint.

Fillers such as talc or China clay may also be used.

The proportion of pigments (including fillers) to polymer is generally such as to give a pigment volume concentration of at least 25 percent, preferably at least 35 percent, in the dry paint film. The upper limit of pigment concentration is the critical pigment volume concentration. Paints having pigment volume concentrations of about 50 percent, for example, have been found very effective for smoothing in sea-water and preventing fouling.

EXAMPLES 2-trifluoromethyl-3-bromo-4-cyano-5-parachlorophenyl pyrrole was used as barnaclecide in all examples.

The binder used in examples 4 to 6 was a copolymer of vinyl chloride and vinyl isobutyl ether commercially available as Laroflex MP 45 (Laroflex is a trade name of BASF).

The algicides used were available commercially as follows:

examples 1 and 4: Seanine (trade mark of Rohm and Haas)
examples 2, 5 and 6: Irgarol 1051 (trade mark of Ciba)
example 3: Preventol A4S (trade mark of Bayer).

Examples 1 to 3 show conventional rosin-based paints; examples 4 to 6 show tin-free paints having a useful life of up to 3 years. (table 1)

TABLE 1

Compositions (parts by weight)

| | Example | | | | | |
|---|---|---|---|---|---|---|
| | 1 | 2 | 3 | 4 | 5 | 6 |
| rosin | 34.0 | 34.0 | 34.0 | 35.0 | 25.5 | 25.5 |
| chlorinated paraffin | 12.5 | 12.5 | 12.5 | — | — | — |
| binder | — | — | — | 13.5 | 9.9 | 9.9 |
| epoxidised soybean oil | — | — | — | 4.7 | 3.5 | 3.5 |
| zinc oxide | 6.4 | 6.4 | 6.4 | 10.5 | 7.7 | 7.7 |
| China clay | 30.7 | 31.4 | 31.9 | — | — | — |
| talc | — | — | — | 7.5 | 29.6 | 18.9 |
| bentone | 3.4 | 3.4 | 3.4 | 4.5 | 3.0 | 3.0 |
| TiO2 | 2.8 | 2.8 | — | — | 5.5 | 20.0 |
| blue dye | 2.8 | 2.8 | — | — | 3.8 | — |
| red dye | — | — | 3.5 | 6.5 | — | — |
| barnaclecide | 2.0 | 2.0 | 2.0 | 3.4 | 2.5 | 2.5 |
| algicide | 5.4 | 4.7 | 6.3 | 14.4 | 9.0 | 9.0 |
| total dry matter | 100 | 100 | 100 | 100 | 100 | 100 |
| ethanol | 1 | 1 | 1 | 1 | 1 | 1 |
| xylene | 42 | 45 | 40 | 59 | 55 | 50 |
| colour | bright blue | bright blue | bright red | bright red | bright blue | bright white |

We claim:

1. Antifouling paint composition comprising an effective amount of at least one algicide, characterised in that it essentially comprises as barnaclecide from 0.5 to 9.9 wt %, based on the total weight of the dry mass of the composition, of at least one 2-trihalogenomethyl-3-halogeno-4-cyano pyrrole derivative substituted in position 5 and optionally in position 1, the halogens in positions 2 and 3 being independently selected from the group consisting of fluorine, chlorine and bromine, the substituent in position 5 being selected from the group consisting of C1-8 alkyl, C1-8 monohalogenoalkyl, C5-6 cycloalkyl, C5-6 monohalogenocycloalkyl, benzyl, phenyl, mono- and di-halogenobenzyl, mono- and di-halogenophenyl, mono- and di-C1-4-alkyl benzyl, mono- and di-C1-4- alkyl phenyl, monohalogeno mono-C1-4-alkyl benzyl and monohalogeno mono-C1-4- alkyl phenyl, any halogen on the substituent in position 5 being selected from the group consisting of chlorine and bromine, the optional substituent in position 1 being selected from C1-4 alkyl and C1-4 alkoxy C1-4 alkyl.

2. Composition according to claim 1, essentially comprising from 1 to 6 wt % of barnaclecide.

3. Composition according to claim 2, essentially comprising from 1.5 to 4 wt % of barnaclecide.

4. Composition according to any one of claims 1 to 3, wherein the derivative is 2-trifluoromethyl-3-bromo-4-cyano-5-parachlorophenyl pyrrole.

5. Composition according to any one of claims 1 to 3, containing at least one component selected from pigments and dyes to have a light or bright colour.

6. A process for preparing an antifouling marine paint composition having a barnaclecide effect, comprising the steps of:

a) mixing together:
(i) a water-erodible binder polymer having protected acid functionality;
(ii) an effective amount of an algicide; and,
(iii) a barnaclecide as defined in any one of claims 1–3; and, b) forming a light color paint with the mixture from step (a).

7. The process of claim 6 wherein the barnaclecide derivative is 2 -trifluoromethyl-3-bromo-4-cyano-5-parachlorophenyl pyrrole.

8. The process of claim 7 further comprising the step of adding to said paint at least one element selected from the group consisting of bright pigments and dyes having a bright color.

* * * * *